(12) United States Patent
Xin et al.

(10) Patent No.: US 8,349,343 B2
(45) Date of Patent: Jan. 8, 2013

(54) TEXTILES WITH CHITOSAN CORE-SHELL PARTICLES

(75) Inventors: John Haozhong Xin, Kowloon (HK); Pei Li, Kowloon (HK); Weijun Ye, Kowloon (HK)

(73) Assignee: The Hong Kong Polytechnic University, Kowloon, Hong Kong SAR (CN)

( * ) Notice: Subject to any disclaimer, the term of this patent is extended or adjusted under 35 U.S.C. 154(b) by 0 days.

(21) Appl. No.: 13/546,442

(22) Filed: Jul. 11, 2012

(65) Prior Publication Data

US 2012/0276796 A1 Nov. 1, 2012

Related U.S. Application Data

(62) Division of application No. 11/045,517, filed on Jan. 31, 2005, now Pat. No. 8,226,962.

(51) Int. Cl.
*A01N 25/34* (2006.01)

(52) U.S. Cl. ............ 424/402; 442/19; 525/242; 523/201

(58) Field of Classification Search .................. None
See application file for complete search history.

(56) References Cited

U.S. PATENT DOCUMENTS

| | | | |
|---|---|---|---|
| 3,960,797 A | 6/1976 | Inman | |
| 6,252,003 B1 | 6/2001 | Kuwahara et al. | 525/242 |
| 6,359,032 B1 | 3/2002 | Kuwahara et al. | 523/201 |
| 6,573,313 B2 | 6/2003 | Li et al. | 523/201 |

*Primary Examiner* — Robert A Wax
*Assistant Examiner* — Hasan Ahmed
(74) *Attorney, Agent, or Firm* — Jacobson Holman PLLC

(57) ABSTRACT

The present invention describes a novel antibacterial treatment on textile materials using polymeric core-shell particles dispersing in water. These particles are prepared from a surfactant-free emulsion polymerization according to the method of U.S. Pat. No. 6,573,313 and have average particle sizes in the range of 100 to 1000 nm in diameter. When applied to a textile article, the particles form a uniform coating, which prevents the growth of bacteria and microbes. The treatment does not affect the fabric mechanical properties, hand feeling and appearance. Antibacterial activity on cotton is maintained even after 50 times of home laundering.

2 Claims, 8 Drawing Sheets

(a)

(b)

(a) Before the treatment (b) After the treatment

TEXTILES WITH CHITOSAN CORE-SHELL PARTICLES

This is a Divisional application of application Ser. No. 11/045,517, filed Jan. 31, 2005, which is hereby incorporated by reference.

FIELD OF THE INVENTION

This invention relates to antibacterial textiles and, in particular, such textiles treated with polymer particles that consist of polymer cores with chitosan shells.

BACKGROUND OF THE INVENTION

Compared with man-made fibers, natural textiles, such as those made from cellulose and protein fibers, are much more vulnerable to microbe attack because of their hydrophilic porous structure and moisture transport characteristics. The use of antibacterial agents to prevent or retard the growth of bacteria on textile articles has been becoming a standard finishing method for textile goods, especially for those used in hospitals, hotels, sports and personal care industries. However, there is an increasing public concerns for possible effects of antibacterial finishing on environmental and biological systems. An ideal textile antibacterial finishing should not only kill undesirable microorganisms and stop the spread of diseases, but also be safe and environmentally benign. Furthermore, the antibacterial function should be maintained for as many cycles through a home laundering process as possible.

Obtained from the shells of crabs, shrimps and other crustaceans, chitosan (CTS) is a non-toxic, biodegradable and biocompatible natural polymer, and has long been used as a biopolymer and natural material in pharmaceutical, medical, papermaking and food processing industries. Because of its polycationic nature, chitosan possesses good antibacterial property against various bacteria and fungi. However, direct coating of chitosan onto textile articles has suffered from four major drawbacks:

1) Chitosan does not dissolve in water but instead only dissolve in acidic aqueous solution. Thus, a considerable amount of acid is used during the chitosan finishing process. This may cause many environmental problems due to the strong odor and corrosive property of acids.
2) The aqueous solution containing dissolved chitosan usually is quite viscous, thus the finishing process is difficult to handle.
3) Chitosan is a rigid material. It affects the fabric hand after coating.
4) Chitosan has strong water-absorption ability due to the presence of many polar groups. Thus the water-repellency of chitosan-treated textile goods is significantly reduced.

Chitosan-containing particles with core-parts and shell-parts have been reported by Kuwahara et al in two U.S. patents (U.S. Pat. Nos. 6,359,032 and 6,252,003) used for other uses such as coloring and deodorizing agents. However, the chitosan molecules on the particle surface are not permanent due to the physical absorption property, thus can be easily released with environmental changes such as pH.

Thus at present, textiles with chitosan particles have not been able to adequately provide an antibacterial action of any permanence without considerable drawbacks.

OBJECTS OF THE INVENTION

Therefore, it is an object of this invention to provide an antibacterial textile and method of producing such that may alleviate or ameliorate at least one or more of the problems as set forth in the prior art or, at a minimum, provide the public with a useful choice.

SUMMARY OF THE INVENTION

Accordingly, in a first aspect the invention may broadly be said to consist in a method of providing an antibacterial finish to a textile including the steps of:
preparing a polymer latex emulsion containing core-shell particles with polymer cores and chitosan shells; and
applying said emulsion to a textile.

Accordingly, in a second aspect, the invention may broadly be said to consist in an antibacterial textile made by the preceding method.

Accordingly, in a third aspect the invention may broadly be said to consist in an antibacterial textile comprising a textile having a finish comprising a polymer latex emulsion containing core-shell particles with chitosan shells.

BRIEF DESCRIPTION OF THE DRAWINGS

Preferred embodiments of the present invention will now be explained by way of example and with reference to the accompanying drawings in which.

DETAILED DESCRIPTION OF THE PREFERRED EMBODIMENT

Figure 1:
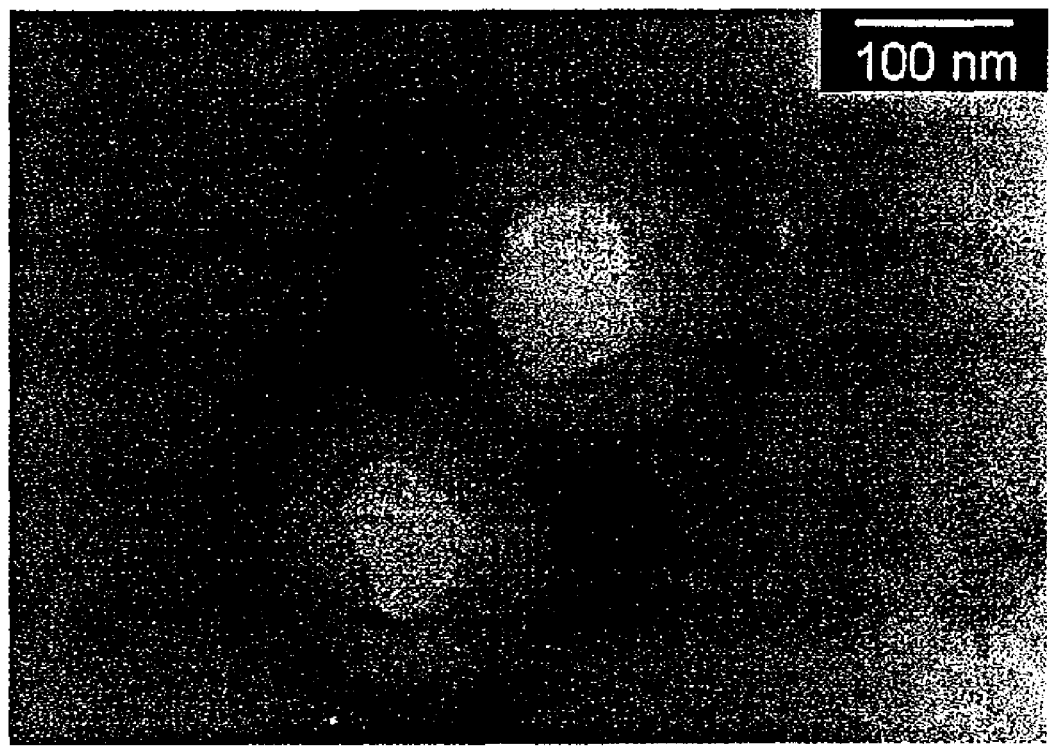
FIG. 1 shows core-shell particles that consist of polymer cores and chitosan shells of this invention.

This invention is now described by way of example with reference to the figures in the following paragraphs. List 1 is a part list so that the reference numerals in the figures may be easily referred to.

Objects, features, and aspects of the present invention are disclosed in or are obvious from the following description. It is to be understood by one of ordinary skill in the art that the present discussion is a description of exemplary embodiments only, and is not intended as limiting the broader aspects of the present invention, which broader aspects are embodied in the exemplary constructions.

The present invention utilizes the antibacterial properties of chitosan applied to textiles. In doing so, the textile may be coated with particles that consist of polymer cores and chitosan shells.

The textiles can be natural, synthetic, and regenerated articles, as well as their blends. Examples are cotton, linen, wool, silk, polyester, nylon, polypropylene, cotton/polyester blends, etc., and their fibers.

In the preparation of this invention, a nanostructured particle may be made containing chitosan in accordance with U.S. Pat. No. 6,573,313 which is incorporated herein by reference.

In the preferred form of the invention, a synthesis of the polymer core-shell particles based on a surfactant-free emulsion copolymerization is provided. The chitosan shell is covalently grafted onto the polymer core, forming a well-defined core-shell nanostructure.

Preferably, the chitosan is dissolved in a diluted acetic acid aqueous solution, together with a vinylic monomer and an alkyl hydroperoxide (ROOH) initiator. No surfactant or emulsifier is involved. This one-pot polymerization is based on a graft emulsion copolymerization in which the alkyl hydroperoxide initiation takes place at the amino groups of chitosan. The resulting amino radicals not only are capable of initiating the graft copolymerization of the vinyl monomer, but also forming amphiphilic copolymers that can act like polymeric surfactants to stabilize the resultant particles. Therefore, there are covalent linkages between the chitosan shell and the polymer core due to the grafting of poly(vinyl) chains onto chitosan backbone. Since amphiphilic graft copolymers formed initially self-assemble into micelle-like micro-domain, many small and uniform particles between 100 to 500 nm in diameter can be produced in a high solid content (up to 30%). Such particles may be seen in FIG. 1.

Further detail of the preferred embodiment is provided in the following examples and description.

Chitosan

The chitosan used in the present invention is poly[β-(1→4)-2-amono-2-deoxy-D-glucopyranose], a deacetylated derivative of chitin. Other modified chitosans with various substituted groups and a part of the deacetylated amino groups can also been used. Such materials can have a wide range of molecular weights ($M_W$) as well as deacetylation degrees (DD). Generally, the antibacterial activity of chitosan increases as the molecular weight and degree of deacetylation of chitosan increase, and decreases over a certain high $M_W$. In the disclosed invention, the $M_W$ of chitosan is higher than 10,000 and the DD is in the range of 10% to 100%. It is desirable to have a medium $M_W$ of chitosan (50,000 to 100,000) with a relatively DD higher than 70%.

Monomer

There is no particular restriction on the monomer of the core as long as it has a reactive vinyl group that can be polymerized by free radicals. Hydrophobic monomers with corresponding polymers having low glass transition temperatures (Tg) are good for particles with soft cores. Hydrophilic monomers can also be used. Depending on the water solubility of core polymers, a crosslinking agent may be needed. A possible core monomer may be vinylic monomer such as an acrylate monomer, an acrylamide monomer, polymerizable nitrile, chloride and fluoride monomers, a styrenic monomer and a diene monomer. It is preferable to monomer with low water solubility under reaction conditions. It is also preferable to a monomer mixture with more than one of the mentioned monomers.

Examples of vinylic monomers include those with one or two carbon-carbon double bonds and substitution groups of hydrogen, alkyl, aryl, heteroaryl, halo, cyano, or other suitable groups.

Examples of acrylate and methacrylate monomers include those of esters which contain vinyl groups directly attached to the carbonyl carbon. They have formula of $CH_2=CH-COOR$ and $CH_2=C(CH_3)-COOR$, where R is alkyl or substituted allyl or other suitable hydrophobic group. Preferred groups for R include $C_1-C_{16}$, more preferably $C_1-C_{12}$ alkyl which may be straight or branched chains, and such groups substituted with one or more substituents chosen from unsubstituted amino, monosubstituted amino or disubstituted amino, hydroxy, carboxy, fluorine atoms, siloxane, or other usual acrylate substituents. Particular acrylate monomers comprise butyl acrylate, ethyl acrylate, isopropyl acrylate, methyl methacrylate, lauryl methacrylate, stearyl methacrylate, and more of these monomers may be used.

Example of (meth)acrylamide monomers includes those of formula $CH_2=CH-CONHR$ and $CH_2=C(CH_3)-CONHR$, where R is as defined above.

Hydroperoxide Initiator

Alkyl hydroperoxides are suitable initiating agents to induce the graft copolymerization of vinyl monomers from chitosan amino groups. Among them, tert-butyl hydroperoxide, cumene hydroperoxide, p-isopropyl cumene hydroperoxide, p-menthane hydroperoxide and pinane hydroperoxide are preferred. The most preferred initiator is the water-soluble tert-butyl hydroperoxide.

Process for Preparing the Polymer Emulsion

The polymer core-shell particles are prepared from a surfactant-free emulsion copolymerization. Chitosan is dissolved in a dilute acetic acid aqueous solution with a chitosan concentration of 0.1 to 10%, preferably in the range of 0.5 to 2% to overcome the high viscosity. Filtration may be necessary to remove any insoluble impurities. Before the polymerization, nitrogen or argon purge may be necessary to remove oxygen in the solution and reaction container. Reaction temperature is in the range of 50 to 100° C., preferably at 80° C. There is no particular limitation for the weight ratio between the monomer and chitosan, preferably at 0.5-50 to 1 (w/w), and ideally at 4-10 to 1 (w/w). The polymerization occurs after the addition of initiator and a white polymer latex emulsion is observed. Concentration of alkyl hydroperoxides can be varied from 0.02 mM to 5.0 mM, preferably with a small amount of ROOH ($\leq$0.2 mM). The polymerization is allowed to react for 24 hours. Normally much shorter time is needed, for example, less than 5 hours.

The core-shell particles prepared from the described emulsion copolymerization are quite uniform, having sizes less than 1 μm, preferably less than 500 nm in diameter. In our invention, the average particle size and the size distribution are measured with a laser diffraction device (Coulter LS-230 Particle Size Analyzer). Scanning Electron Microscopy (SEM) (Leica Stereoscan 440 SEM) is used to image the particle morphology. The particle internal core-shell structure is revealed by an FEITACNAIR scanning transmission electron microscope (STEM).

Process for Antibacterial Treatment

The polymer emulsion prepared as disclosed can be applied to various textile materials by padding, coating or spray, preferably by padding at room temperature. It is preferred that the material wet pick-up is around 80~100 wt %. A further drying or curing process may be necessary and the conditions depend on the nature of the textile. For example, padded cotton needs 5-min drying in an oven at 100° C., followed by 4-min curing at 150° C. For nonwoven polypropylene (PP), 3-min drying at 100° C. is enough after padding. Rinsing with water is recommended for all finished samples. Crosslinking agents may or may not be added in the padding solution, depending on the requirement. The treatment is suitable for natural and synthetic fabric, including cotton, linen, wool, silk, polyester, nylon, polypropylene, and cotton/polyester blends, etc., as well as their fibers. It is reasonable to assume that the disclosed invention is also useful for coatings on a solid surface, such as toys and furniture, for antimicrobial purpose.

Antibacterial Test

The antibacterial mechanism of chitosan is a non-leaching type, which means that chitosan cannot be released from the substrate to the medium during inhibition. Therefore, it is recommended that the Shake Flask Method (Corporate Test Method 0923) and the ASTM-E-2148-01 are preferable to evaluate the antibacterial activity. Both methods are specially designed for non-releasing antibacterial treated specimens under dynamic contact conditions. The test determines the reduction in the number of bacterial cells in one hour (or several hours) shaking flask containing treated specimen to provide quantitative data. A gram positive bacterium, *S. aureus* (ATCC 6538), commonly found on the human body, may be used as the testing bacterium. The antimicrobial efficacy of tested fabrics can be expressed as percentage bacterial reduction calculated from to the following equation:

$$R=(B-A)/B \times 100,$$

where R is the percentage bacterial reduction, B and A are the number of live bacterial cells in the flask before and after shaking.

EXAMPLES

The following examples are provided in order to illustrate the practice of the invention, but are not to be constructed to limit the scope of the invention.

Example 1

Synthesis of Chitosan/Poly(n-Butyl Acrylate) (CTS-PBA) Particles

A 500 mL round-bottomed, three-necked flask equipped with a magnetic stirring bar, a condenser, and a nitrogen inlet was immersed in an oil bath. In a typical run, 100 mL of 0.6% acetic acid in solution was added into the flask, followed by the addition of 0.5 g chitosan. The flask was then heated to 60° C. and the solution was stirred continuously. After the dissolution of chitosan was completed, filtration might be necessary to remove any residues. Then the solution was heated to 80° C. under a nitrogen purge. Purified monomer (2 g) was added, followed by a quick addition of 1 mL of TBHP initiator solution (20 mM). Within minutes, the reaction medium became aggressively white and was finally stabilized as milky-white latex solution under stirring. Polymerization was held at 80° C. for 5 hours, and a slow nitrogen purge was maintained throughout the reaction. After completion, the white latex dispersion was cooled down to room temperature and stored for finish procedure. Monomer conversion was determined gravimetrically.

Example 2

Synthesis of Chitosan/Poly(N-isopropylamide) (CTS-PNIPAM) Particles

For the preparation of CTS-PNIPAM particles, the procedure is similar to Example 1 except 1% of N—N'-methylenebisacrylamide crosslinker (MBA, based on the weight of NIPAM) was added as a crosslinking agent for polyNIPAM core.

Characterization of CTS-PBA Particles

Figure 2:
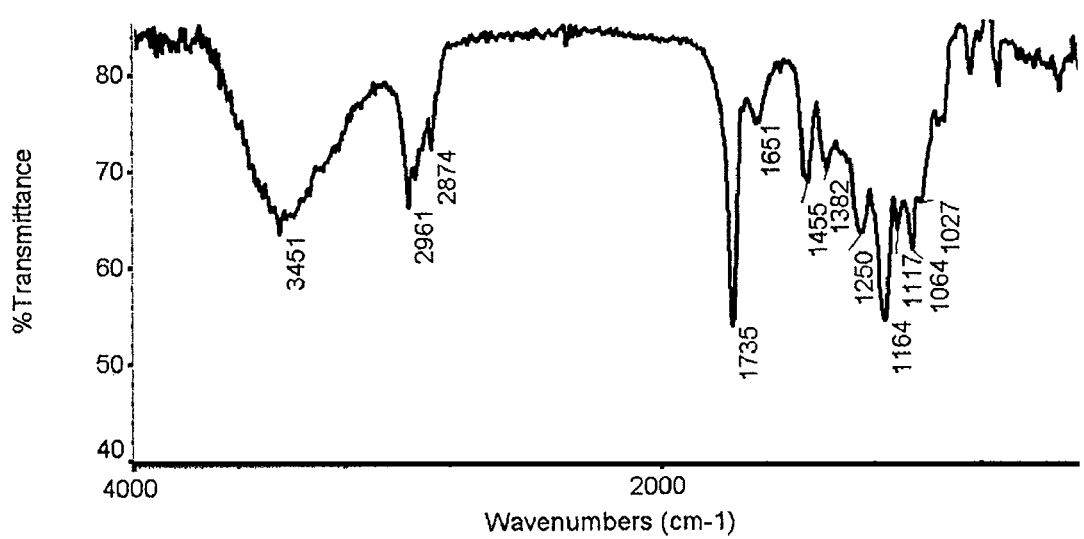
FIG. 2 shows the Fourier transform infrared (FTIR) spectrum of chitosan-g-poly(n-butyl acrylate) (CTS-PBA) graft copolymer.

The poly(n-butyl acrylate) homopolymer and the chitosan-g-poly(n-butyl acrylate) graft copolymer were isolated using Soxhlet extraction with 1% acetic acid solution followed by chloroform. The PBA core comprises 67% grafted poly(n-butyl acrylate) and 33% poly(n-butyl acrylate) homopolymer. The FTIR spectrum (FIG. 2) of the graft copolymer shows strong carbonyl peaks at 1735 $cm^{-1}$, and amino peak at 3451 $cm^{-1}$, indicating the presence of both poly(n-butyl acrylate) and chitosan.

Figure 3:
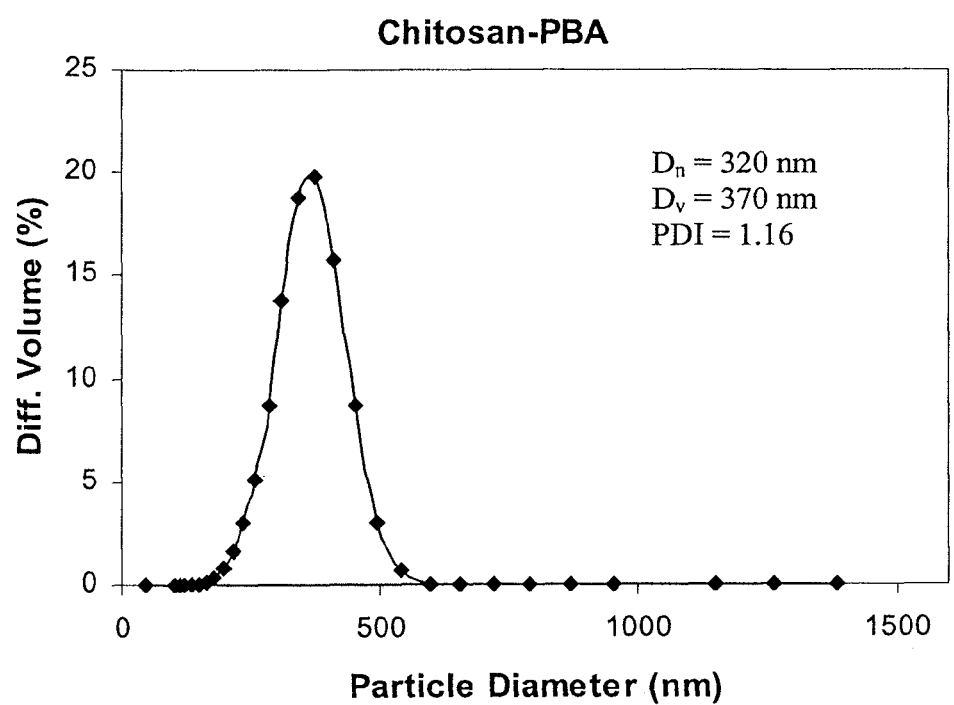
FIG. 3 shows the CTS-PBA particle size and distribution by dynamic light-scattering, $D_n$=number average diameter, $D_v$=volume average diameter, PDI=$D_v/D_n$.

Measurements of particle size and distribution as shown in FIG. 3 indicate that the average number particle diameter of CTS-PBA particles was 320 nm, with narrow particle size distribution (polydispersity index, $D_v/D_n=1.16$).

Figure 4:
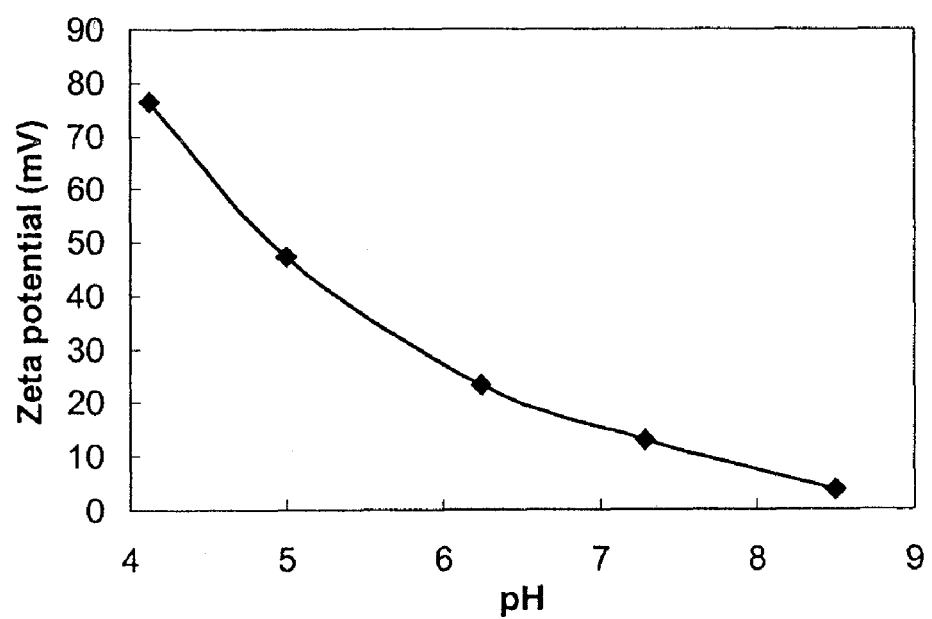
FIG. 4 shows the pH dependence of the zeta-potential of CTS-PBA particles in a 1 mM NaCl solution at room temperature.

Particle surface charge was determined by ξ-potential measurement. FIG. 4 shows the ξ-potential of CTS-PBA latex as a function of pH in a 1 mM NaCl solution at 25° C. As pH increased, the positive value of the particles decreased, indicating the labile cationic chitosan coated on the particle surfaces.

Figure 5:
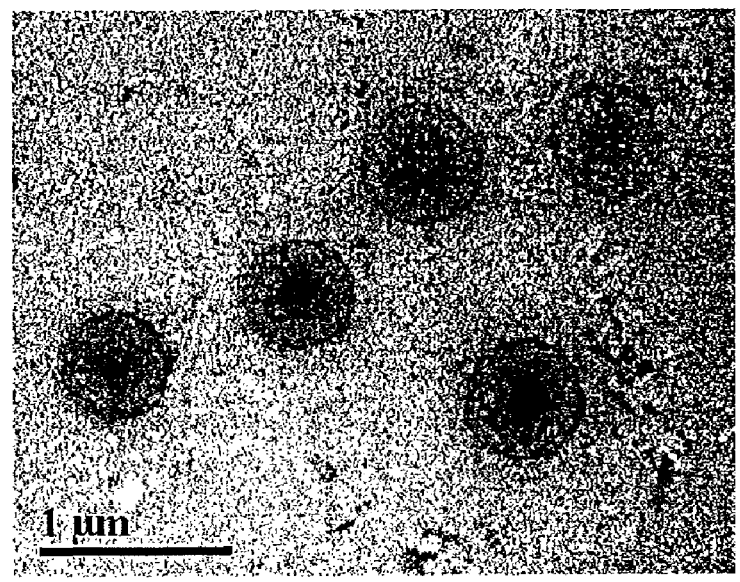
FIG. 5 shows the transmission electron microscope (TEM) images of CTS-PBA core-shell particles.
Figure 5:
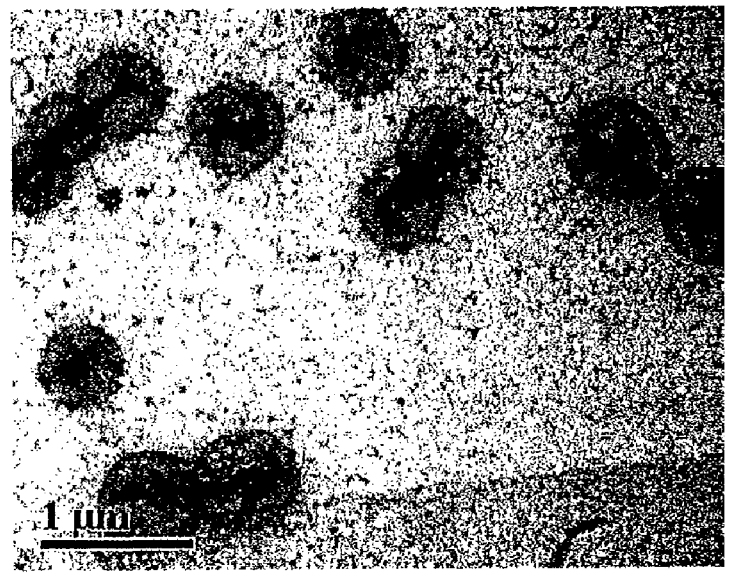

With careful staining of the CTS-PBA particles, the nanostructure of the particles was clearly revealed with TEM images. FIG. 5 shows that the CTS-PBA particles are spherical and have well-defined core-shell morphology where poly(n-butyl acrylate) cores are coated with chitosan shells. It also shows that the CTS-PBA particles are so soft that particles are deformed when they are contact with each other (FIG. 5b).

Example 3

Preparation of Antibacterial Cotton Fabrics

The antibacterial finish is based on the conventional pad-dry-cure method. Each fabric sample (~20×40 cm) was washed with nonionic detergent before finishing, then immersed into CTS-PBA or CTS-NIPAM emulsions with or without a crosslinker dimethylolhydroxyetheneurea (DMDHEU, 0.3 wt % with a catalytic amount of magnesium chloride) for 3~5 minutes, and padded through a laboratory pad machine (Rapid Vertical Padder, Taiwan) under a nip pressure of 1 kg/$cm^2$ for a wet pick-up of ~100%. The dip-pad procedure was repeated one more time, then the twice-padded samples were dried in an oven at 100° C. for 5 minutes and subsequently cured at 150° C. for 4 minutes. After rinsing with running tap water, the treated samples were dried and ready for further tests.

Figure 6:
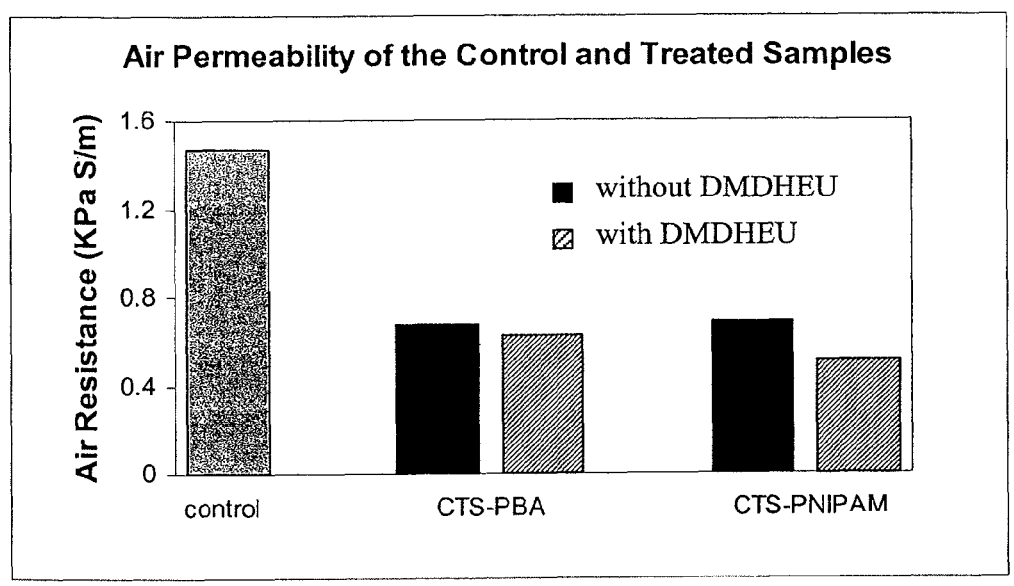
FIG. 6 shows the air resistance of untreated and treated cotton fabrics with CTS-PBA and chitosan-poly(N-isopropyl acrylamide) (CTS-PNIPAM) particles.

Fabric mechanical properties, such as air permeability, handling, and tensile strength, are shown in FIG. 6, Table 1 and Table 2, respectively. The results suggest that all particles-treated samples have improved air permeability regardless of the DMDHEU binder. In both warp and weft directions the cotton fabric tensile strength decreased after the latex modification. Nevertheless, the change was not significant. All fabrics still maintained at least 75% of their original tensile strength. The addition of the crosslinker DMDHEU could weaken the fabric tensile property as when a small amount of DMDHEU was added, more decreases in fabric tensile strength along both warp and weft directions were observed (Table 2).

Results on fabric hand (Table 1) showed that the latex finish could increased the values of fabric bending rigidity (B) and hysteresis of bending moment (2HB) in both machine (warp) and cross (weft) directions. Depending on the core flexibility and the padding solution with or without a crosslinker, the increase in fabric stiffness was quite different. While fabrics became much stiffer after finishing with the hardcore CTS-PNIPAM latexes, the soft CTS-PBA treated cotton had relatively small changes in both bending rigidity and bending hysteresis. Moreover, we found that the CTS-PBA padded sample had a better fabric hand than the fabric padded from 0.5 wt % chitosan solutions (Table 1).

Example 3

Antibacterial Test

Figure 7:
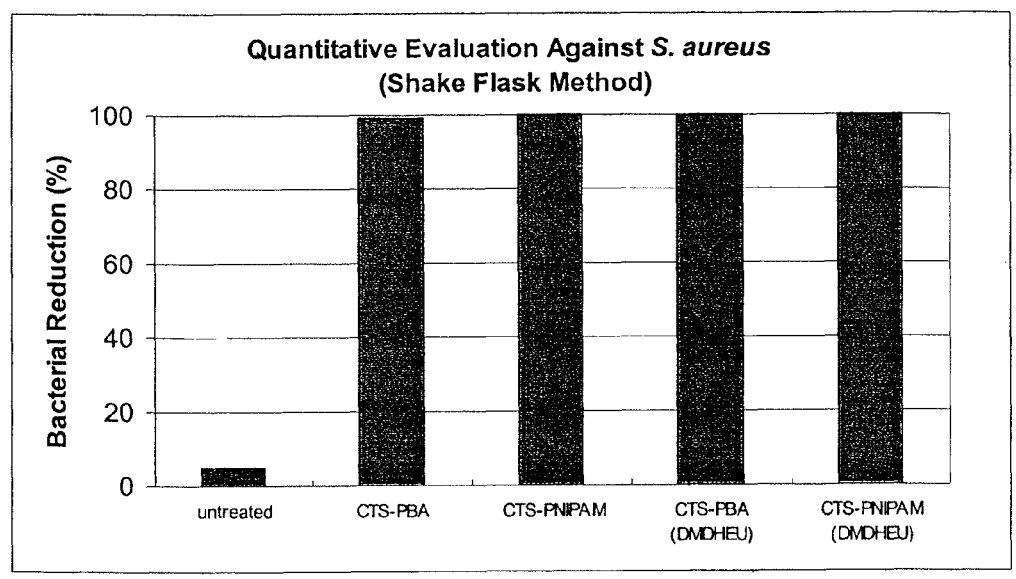
FIG. 7 shows the bacterial reductions of antimicrobial specimens treated with CTS-PBA and CTS-PNIPAM in the presence or absence of crosslinker.
Figure 8:
FIG. 8 shows the test agar plates from the fabrics before and after the antibacterial treatment.
Figure 8:
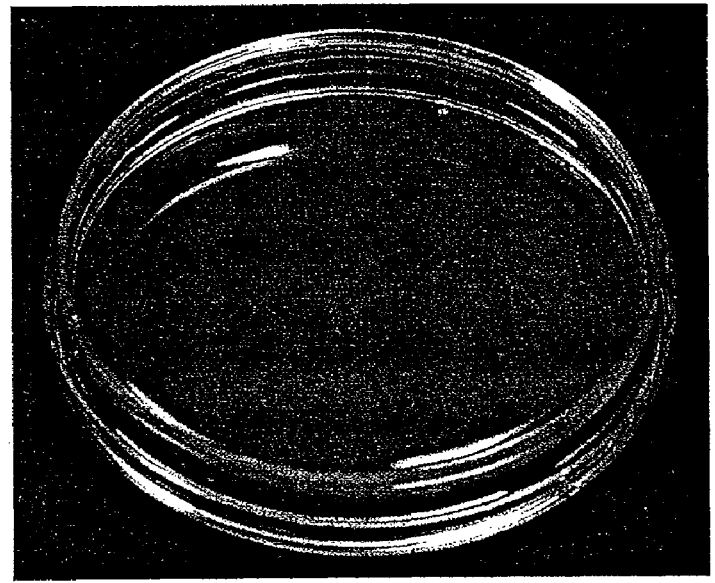

In this procedure, sample fabrics (1±0.1 g), cut into around 0.5×0.5 cm, were dipped into a test flask containing 50 mL of 0.5 mM PBS (monopotassium phosphate) culture solution with a S. aureus (ATCC 6538) cell concentration of $1.0-1.5 \times 10^4$/mL. The flask was then shaken at 250 rpm on a rotary shaker at 37° C. for 1 h. Before and after the shaking, 1 mL of the test solution was extracted, diluted and spread onto an agar plate. After 24 h of incubation at 37° C., the number of colonies formed on the agar broth was counted and the number of bacterial cells (A or B) in the testing flask was calculated. FIGS. 7 & 8 are the results of antibacterial tests on cotton fabrics before and after the treatment. Besides cotton, antibacterial test on other modified textiles is summarized in Table 3. All results indicated that the core-shell particles with chitosan antibacterial shells had excellent antimicrobial activity on textile materials.

Example 4

Washfastness

To check the durability of antimicrobial treatment, accelerated wash fastness was evaluated based on the AATCC Test Method 61-1996. An AATCC standard wash machine (Atlas Launder-Ometer) and detergent (AATCC Standard Detergent WOB) was used. Samples were cut into 5×15 cm swatches and put into a stainless steel container with 150 mL of 0.15 w/v % WOB detergent solution and 50 steel balls (0.25 in. in diameter) at 49° C. for various washing time to mimic 5, 20 and 50 wash cycles of home/commercial launderings. Results of antibacterial durability of cotton fabric after different laundry cycles are summarized in Table 4. All samples maintained high antibacterial efficacy (>90%) after 50 times of wash regardless of the DMDHEU crosslinker.

Thus it can be seen that the description and examples give rise to a textile coated or treated with chitosan in which the chitosan-based core-shell particles once applied to a textile offer the following advantages:

1) The particle consists of a well-defined core-shell nanostructure where the polymer core can be flexible material. Thus the polymer core can provide a flexible coating with a good water-repellency.
2) Since the chitosan is covalently bounded on the polymer core, not dissolved, viscosity of the particle dispersion is low even with high content of chitosan. Thus the coating is more uniform and the finishing process is much easier to handle.
3) The particles are in nano-sized range, and form ultrathin film on textile surface. Therefore, the fabric hand and appearance are not affected very much by the coating.
4) The chitosan shell functions not only as an antibacterial agent, but also provides functional groups to strongly bind with textile material. Thus the coating is enduring.

The core-shell particles may also be used as antibacterial coatings or additives in a wide variety of applications that may have fabric on them or are similar to textiles in nature such as cotton balls. They may include items such as toys, furniture, interior textiles, medical/hospital materials, and cosmetic/personal care products. Examples of such applications include the following:

Solid objects: toys, containers, furniture and the like;

Interior textiles: drapes, curtains, carpets, air filters and the like;

Medical/hospital materials: surgical gowns, masks, sutures, hospital sheets, pillows and the like;

Personal care/cosmetic products: diapers, feminine products, deodorants, cotton balls, cotton swabs and the like.

While the preferred embodiment of the present invention has been described in detail by the examples, it is apparent that modifications and adaptations of the present invention will occur to those skilled in the art. Furthermore, the embodiments of the present invention shall not be interpreted to be restricted by the examples or figures only. It is to be expressly understood, however, that such modifications and adaptations are within the scope of the present invention, as set forth in the following claims. For instance, features illustrated or described as part of one embodiment can be used on another embodiment to yield a still further embodiment. Thus, it is intended that the present invention cover such modifications and variations as come within the scope of the claims and their equivalents.

TABLE 1

Bending rigidity (B) and bending hysteresis (2HB) of untreated and treated cotton fabrics

| | Fabric Direction | | | |
|---|---|---|---|---|
| | Warp | | Weft | |
| Sample | B-MEAN [gf.cm$^2$/cm] | 2HB-MEAN [gf.cm/cm] | B-MEAN [gf.cm$^2$/cm] | 2HB-MEAN [gf.cm/cm] |
| Untreated | 0.0353 | 0.0360 | 0.0720 | 0.0658 |
| CTS-PBA | 0.0604 | 0.0310 | 0.1756 | 0.0796 |
| CTS-PNIPAM | 0.1375 | 0.0916 | 0.3754 | 0.2314 |
| CTS-PBA (DMDHEU) | 0.0878 | 0.0518 | 0.2576 | 0.1396 |
| CTS-PNIPAM (DMDHEU) | 0.1425 | 0.1191 | 0.3620 | 0.2835 |
| CTS | 0.0783 | 0.0508 | 0.2860 | 0.1361 |
| CTS (DMDHEU) | 0.1436 | 0.1007 | 0.3294 | 0.2195 |

TABLE 2

Break tensile strength and elongation of treated and untreated cotton fabrics

| | Tensile Direction | | | | | |
|---|---|---|---|---|---|---|
| | WARP | | | WEFT | | |
| Sample | Break force (N) | Strength maintained (%) | Break strain (%) | Break force (N) | Strength maintained (%) | Break strain (%) |
| Untreated | 377.5 | — | 17.8 | 219.2 | — | 15.0 |
| CTS-PBA | 364.6 | 96.6 | 20.7 | 168.6 | 76.9 | 12.3 |
| CTS-PNIPAM | 361.8 | 95.8 | 19.5 | 210.6 | 96.1 | 14.1 |
| CTS-PBA (DMDHEU) | 305.1 | 80.8 | 16.9 | 164.4 | 75.0 | 13.5 |
| CTS-PNIPAM (DMDHEU) | 356.8 | 94.5 | 18.6 | 197.9 | 90.3 | 13.9 |

TABLE 3

Antibacterial reductions (%)* of various fabrics after the modification with CTS-PBA and CTS-PNIPAM particles

| Fabric | untreated | CTS-BA treated | CTS-NIPAM treated |
|---|---|---|---|
| silk | 2.9 | 100.0 | 95.9 |
| polypropylene | 0.0 | 94.4 | 100.0 |
| linen | 0.0 | 90.6 | 99.2 |
| polyester | 4.4 | 91.2 | 98.8 |
| nylon | 0.0 | 94.9 | 99.9 |
| Polyester/cotton, 65/35 | 2.6 | 97.1 | 96.9 |
| diacetate | 4.2 | 97.1 | 100.0 |
| wool | 3.8 | 99.4 | n/a |

*Antibacterial reductions with standard deviation of ±4.5%

TABLE 4

Antibacterial activity of treated cotton after different laundering cycles (%: bacterial reduction, with ±5% error bar)

| wash cycles | 0 | 5 | 20 | 50 |
|---|---|---|---|---|
| CTS-PBA | 99.0 | 89.2 | 92.6 | 98.7 |
| CTS-PNIPAM | 100 | 98.3 | 98.3 | 98.7 |
| CTS-PBA (DMDHEU) | 100 | 100 | 99.8 | 96.7 |
| CTS-PNIPAM (DMDHEU) | 100 | 97.7 | 99.8 | 97.9 |

The invention claimed is:

1. An antibacterial textile made by the method comprising the steps of:
preparing a polymer latex emulsion containing chitosan-based polymeric core-shell particles; and
applying said emulsion to a textile, the emulsion being prepared by a surfactant-free emulsion polymerization in which chitosan is first dissolved in a diluted acid solution with a concentration of 0.1 to 10%, followed by the addition of a vinyl monomer and a hydroperoxide initiator, the chitosan having a molecular weight of 50,000 to 100,000; and deacetylation degree of 10% to 100%; and a weight ratio of vinyl monomer to chitosan is between 0.5-50 to 1 (w/w).

2. An antibacterial textile comprising a textile having a finish comprising the polymer latex emulsion containing polymeric core-shell particles as set forth in claim 1.

* * * * *